US008774904B2

(12) United States Patent
Birngruber et al.

(10) Patent No.: US 8,774,904 B2
(45) Date of Patent: Jul. 8, 2014

(54) DEVICE WITH AN OCT SYSTEM FOR EXAMINING AND TREATING LIVING TISSUE BY MEANS OF HEATING OF THE TISSUE BY ABSORBING ELECTROMAGNETIC RADIATION

(75) Inventors: Reginald Birngruber, Luebeck (DE); Ralf Brinkmann, Luebeck (DE); Gereon Huettmann, Luebeck (DE); Heike Mueller, Hamburg (DE)

(73) Assignee: Medizinisches Laserzentrum Luebeck GmbH, Luebeck (DE)

( * ) Notice: Subject to any disclaimer, the term of this patent is extended or adjusted under 35 U.S.C. 154(b) by 92 days.

(21) Appl. No.: 13/642,212
(22) PCT Filed: Apr. 16, 2011
(86) PCT No.: PCT/DE2011/000419
§ 371 (c)(1),
(2), (4) Date: Dec. 26, 2012
(87) PCT Pub. No.: WO2011/134454
PCT Pub. Date: Nov. 3, 2011

(65) Prior Publication Data
US 2013/0102894 A1 Apr. 25, 2013

(30) Foreign Application Priority Data
Apr. 28, 2010 (DE) .......................... 10 2010 018 679

(51) Int. Cl.
*A61B 6/00* (2006.01)
(52) U.S. Cl.
USPC .......................................... 600/476; 600/473
(58) Field of Classification Search
USPC ................................................ 600/473–480
See application file for complete search history.

(56) References Cited

U.S. PATENT DOCUMENTS 6,830,567 B2 * 12/2004 Schuele et al. ..................... 606/4
8,244,334 B2 * 8/2012 Huang et al. ................... 600/476

(Continued)

FOREIGN PATENT DOCUMENTS

| DE | 10135944 A1 | 2/2003 |
| WO | WO 2009108950 A2 | 9/2009 |

OTHER PUBLICATIONS

Müller et al., "Imaging of temperature distribution and retinal tissue changes during photocoagulation by high speed OCT", *Proceedings of SPIE*, Jan. 2011, pp. 1-7, vol. 7889.

(Continued)

*Primary Examiner* — Sanjay Cattungal
(74) *Attorney, Agent, or Firm* — Saliwanchik, Lloyd & Eisenschenk

(57) ABSTRACT

A device for examining or treating living tissue by means of local heating of the tissue by absorbing electromagnetic radiation, with at least one radiation source emitting electromagnetic radiation, a control unit for controlling the irradiation parameters of the radiation source, and at least one FD-OCT apparatus with a light source emitting a measurement light for illuminating that tissue region in which the electromagnetic radiation is absorbed by the tissue, characterized by a computational unit for carrying out the following steps: determining the depth-resolved tissue velocity in the radiation direction of the measurement light at a predetermined measurement point of the tissue from the phase information from the FD-OCT interference light, integrating the established tissue velocity over time, differentiating the calculated time integral with respect to space, and displaying the spatial derivative as a function of space and time and/or feeding the spatial derivative as a function of space and time to an evaluation module and/or feeding the spatial derivative as a function of space and time to the control unit.

18 Claims, 3 Drawing Sheets

(56) References Cited

U.S. PATENT DOCUMENTS

| | | | |
|---|---|---|---|
| 8,285,368 B2* | 10/2012 | Chen et al. | 600/478 |
| 8,433,393 B2* | 4/2013 | Sharma et al. | 600/477 |
| 2005/0171438 A1* | 8/2005 | Chen et al. | 600/476 |
| 2009/0005691 A1* | 1/2009 | Huang et al. | 600/476 |
| 2011/0009752 A1* | 1/2011 | Chen et al. | 600/478 |
| 2011/0071404 A1* | 3/2011 | Schmitt et al. | 600/479 |
| 2011/0178413 A1* | 7/2011 | Schmitt et al. | 600/478 |
| 2012/0130253 A1* | 5/2012 | Nadkarni et al. | 600/476 |
| 2013/0072805 A1* | 3/2013 | Schmitt et al. | 600/479 |

OTHER PUBLICATIONS

Vakoc et al., "Real-time microscopic visualization of tissue response to laser thermal therapy", *Journal of Biomedical Optics*, Mar./Apr. 2007, pp. 1-3, vol. 12, No. 2.

Yeh-Chan Ahn et al., "Quantification of a three-dimensional velocity vector using spectral-domain Doppler optical coherence tomography", *Optics Letters*, Jun. 2007, pp. 1-3, vol. 32, No. 11.

* cited by examiner

DEVICE WITH AN OCT SYSTEM FOR EXAMINING AND TREATING LIVING TISSUE BY MEANS OF HEATING OF THE TISSUE BY ABSORBING ELECTROMAGNETIC RADIATION

CROSS REFERENCE TO A RELATED APPLICATION

This application is a National Stage Application of International Application Number PCT/DE2011/000419, filed Apr. 16, 2011; which claims priority to German Application No. 102010018679.1, filed Apr. 28, 2010; all of which are incorporated herein by reference in their entirety.

The invention relates to a device for examining and possibly for treating living tissue by means of local heating of the tissue by absorbing electromagnetic radiation, for example of laser light or microwave radiation. The invention further relates to a device for measuring tissue properties in real time. The invention furthermore relates to a device for the feedback dosimetry control of the therapeutic radiation source.

The analysis of the expansion of an absorber and the pressure wave emitted therewith after application of a short laser pulse is described in Sigrist M. W., "Laser Generation of Acoustic Waves in Liquids and Gases", Journal of Applied Physics 60(7):R83-R121, 1986.

On this basis, the optoacoustic temperature measurement on the retina was developed as it is illustrated in DE 101 35 944 C2. Here pressure waves are generated by repetitively irradiating using short laser pulses, the pressure waves propagate through the living eye and can be detected as pressure transients on the cornea using an ultrasound sensor (for example piezo element). The amplitudes of the pressure transients for example permit conclusions to be drawn as to the temperature at the eyeground—at least averaged over the irradiated area that forms the starting point of the pressure wave.

The method according to DE 101 35 944 C2 is real-time-capable and thus is suited for controlling the therapeutically active radiation source (here: laser). However, it is not an imaging method (i.e., it does not permit any spatially resolved measurement), is not non-contacting and above all its applicability is limited to the regime of the thermoelastic tissue changes. In the case of persistent damage arising, for example coagulations or blistering, then as a matter of principle the optoacoustic signals can no longer be interpreted and typically show a rather random behavior.

So that tissue changes by absorbing electromagnetic radiation can be observed consistently from the area of thermoelastic expansion up to arbitrary tissue damage, the application of the known optical coherence tomography (OCT) recommends itself. This is an imaging method; it is non-contacting and nowadays can be carried out very fast. An OCT measurement (also A scan) is carried out locally where the measurement light beam is directed, the measurement light being back-scattered at different depths of the sample. The returning measurement light is superposed with a reference light beam, and the measured interference light permits among others to calculate the distribution of the scattering strengths along the back-scattered direction (equals original direction of the beam) of the measurement light. Typical measuring depths of OCT systems are between 0.5 and 2 millimeters. The measurement light beam can be deflected laterally by means of an electronic scanner, and a predetermined line or area can be guided in a scanning manner across the sample (also B scan). Thus the behavior of a selectable sample slice or volume of limited depth can be observed, in particular a living tissue. The main applications of the OCT are therefore in ophthalmology, dermatology and in endoscopy.

WO 01/80792 A2 therefore teaches that reflectivity depth profiles of a biological sample are to be determined and evaluated using a high measuring speed by means of OCT to detect tissue changes as a result of laser therapy. WO 01/80792 A2 however does not give any hints as to which tissue parameters are relevant for examining the irradiation effects or even for controlling the therapeutic radiation and how corresponding interpretations or measures are to be derived from the measured profiles. To this extent, the specification only teaches that therapeutic radiation is to be accompanied by OCT measurements and totally leaves it to the reader to determine the measured data for himself.

In view of DE 101 35 944 C2, the thermomechanic properties of the living tissue are made the focus for this purpose.

Determining mechanical properties in particular by means of OCT measurements is the subject-matter of OCT elastography (OCE). For example, the work by Liang et al., "Optical micro-scale mapping of dynamic biomechanical tissue properties", Vol. 16, No. 15, OPTICS EXPRESS, 11052 pp. (2008), reveals a method for determining the biomechanical properties of biological ex vivo samples by imaging, which examines the microscopic, spatially resolved movement of the samples when excited mechanically, for example by means of piezo elements. Here the temperature of the sample can be set in a targeted manner. OCE leaves the sample unchanged (non-destructive measurement) and relies on a precise control of the mechanical excitation.

Here, OCE is suited for measurements on a living patient only to a limited extent, since then inevitable own movements occur and in addition the controlled mechanical excitation cannot always be performed directly at the target tissue (see for example WO 2007/059292 A2, where however no OCT but a laser velocimeter is used on reflecting surfaces to measure the response to mechanical excitations).

The work by Liang et al. gives two valuable hints: on the one hand, one is to look at the measurable OCT phases to determine local tissue movements, and on the other hand, use of a spectral domain or also Fourier domain (FD) OCT is recommended for phase measurement.

DE 43 09 056 A1, for example, reveals an FD-OCT. Here, light from a short-coherent light source is scattered in the sample in a plane having a distance z to a reference plane (z=0) and superimposed with back-scattered light from the reference plane. A constructive or destructive interference occurs for any fixed distance z of the planes depending on which of the irradiated wavelengths $\lambda$ is observed. When using short-coherent (broadband) light, e.g. from a superluminescent diode, the interference light is split up spectrally and usually imaged onto a sensor line or a comparable device. This permits measuring the distribution I(k), $k=2\pi/\lambda$ as a spatial distribution on the sensor line. The Fourier transformation of this distribution leads to the depth-dependent scattering strength S(z). Apart from this design, called a spectral radar, a further design of the FD-OCT that is also called swept-source OCT (SS OCT), on a fast tunable laser having a photodetector that measures the spectrum of the interference at the output of the interferometer.

The work by Vakoc et al., "Real-time microscopic visualization of tissue response to laser thermal therapy". J. Biomed. Opt., Vol. 12(2), p. 020501-1 (2007) finally is the closest prior art. It shows in particular the measurability of tissue velocities from the phase signal of an FD-OCT while simultaneously absorbing laser radiation. The targeted local heating leads to a denaturing of ex vivo tissue, and the correlation between the OCT phase signal and the damage depth is demonstrated using histological findings for different exposition times. Here the OCT phases can be measured in real time.

This confirms that the progress when treating biological tissue by absorbing electromagnetic radiation can in principle be observed within the measurable phase data of an FD-OCT.

Even Vakoc et al. still does not answer the questions as to the handling of own movements during the in vivo application and as to a suitable observable which can be used to discriminate thermoelastic tissue expansions from persistent tissue expansions in real time—and surely only by subsequent histological examination.

The object of the invention is to specify a device for examining and possibly treating living tissue by means of heating by absorbing electromagnetic radiation, the device determining thermo-mechanical tissue effects and, if required, also controlling the radiation source on the basis of the measured data.

The object is achieved by a device according to claim 1. The sub-claims specify advantageous designs.

The inventive device comprises an electromagnetic radiation source (e.g. a laser, a flash lamp, a microwave source or similar) and a control unit for controlling the irradiation parameters of the radiation source (in particular intensity, irradiation length, repetition rate, pulse energy, luminosity, etc.). The device further exhibits at least one FD-OCT apparatus. The at least one FD-OCT apparatus comprises a polychromatic light source, optical components for illuminating the tissue at predetermined measuring sites and for guiding back the light returning from the measuring sites into a measuring unit. In the measuring unit that likewise is part of the FD-OCT apparatus, the returning light is superimposed with a reference light beam. The measuring unit comprises a detector that detects the spectral intensity distribution at the output of the interferometer (typically a linear line sensor in the case of the spectral radar or a photodiode arrangement in the case of an SS-OCT).

The inventive device furthermore exhibits a computational unit that carries out the following tasks:
a. Reading the measurement data of at least one detector of the at least one FD-OCT apparatus for a predetermined measuring site on the sample surface;
b. Calculating the scattering strengths and phases from the sensor data along the at least one irradiation direction of the FD-OCT measurement light;
c. Calculating the local tissue velocities along at least one irradiation direction from the predetermined phases;
d. Repeating the steps a. to c. in predetermined intervals for the same measuring site;
e. Integrating the local velocities determined under c. over time by summing the data determined under c. over a predetermined multiplicity of repetitions according to step d.;
f. Differentiating the integrals calculated under e. according to at least one coordinate of the coordinate system indexing the locations of the measured scattering strengths and phases;
g. Providing the data calculated according to step f. for outputting (e.g. on a display device) and/or for further evaluation and decision-making for controlling the control unit of the radiation source.

Step g. mentioned last is explained further below.

The inventive device thus goes further than Vakoc et al.—in its simplest design—to the extent that it additionally carries out at least the steps e. and f. Even though initially these are method steps, the implementation in a computational unit is unavoidable since the executability of the dosimetry control that is explained later presupposes that the calculations have to be carried out within fractions of a second. This would not be possible without automation.

The invention reveals a new plane of interpreting measuring data that is to be explained in detail below. This new interpretation results in expansion options of the device that likewise are a subject matter of this invention.

The invention is also explained using figures, in which.

Today's FD-OCT systems permit an A scan—the recording of a single depth profile for a single measuring site—within 10 µs. The depth resolution of the measurement amounts to approximately 10 µm, and the measurement depth of an FD-OCT typically amounts to 500-1000 µm and is also a function of the properties of the sample.

Figure 1:
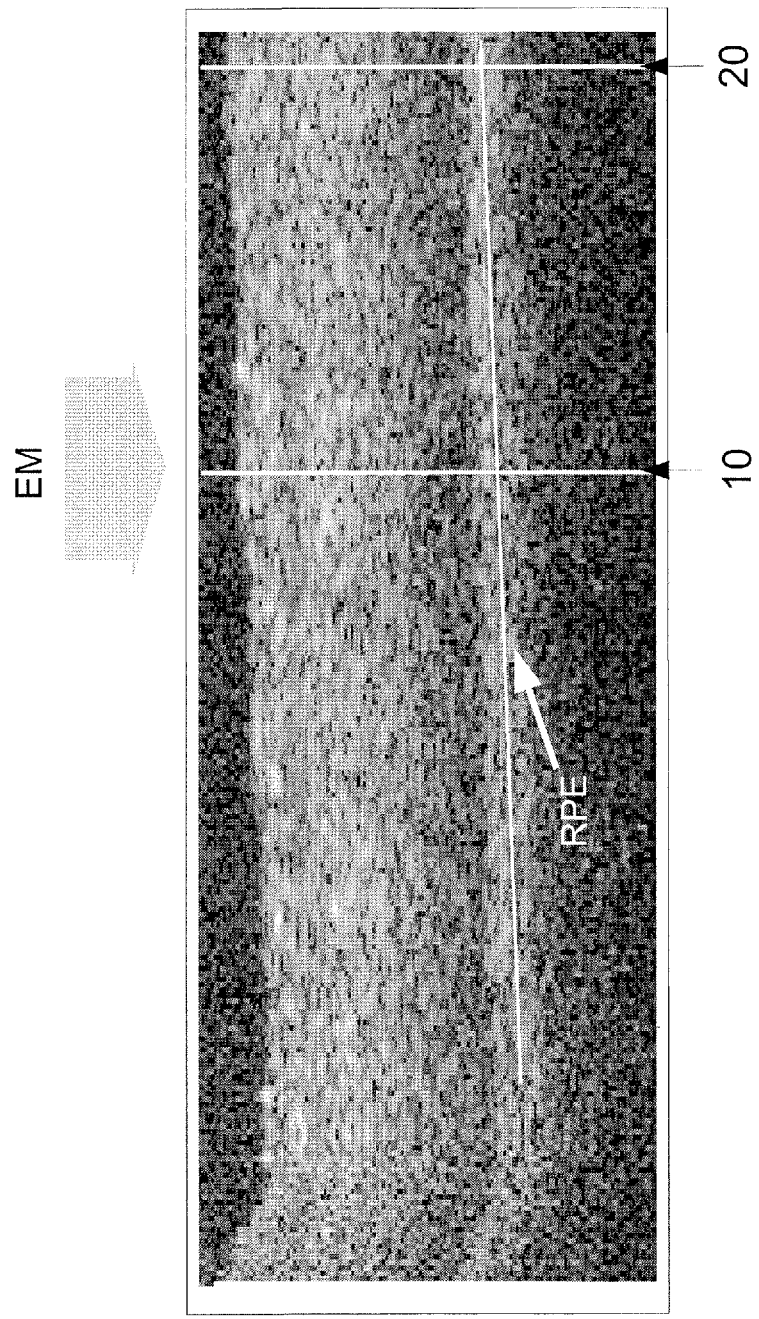
FIG. 1 shows an intensity image of the scattered-strength distribution in the cornea of the eye with the RPE layer that is marked by a white horizontal line, recorded using an FD-OCT line scan. Vertical white lines characterize selected depth profiles.

FIG. 1 shows a typical FD-OCT image that results when the measuring-light illumination is guided along the surface of a retina (line scan). The figure shows the measurable scattering strengths as an intensity plot, lighter pixels indicating higher scattering strengths.

Figure 4:
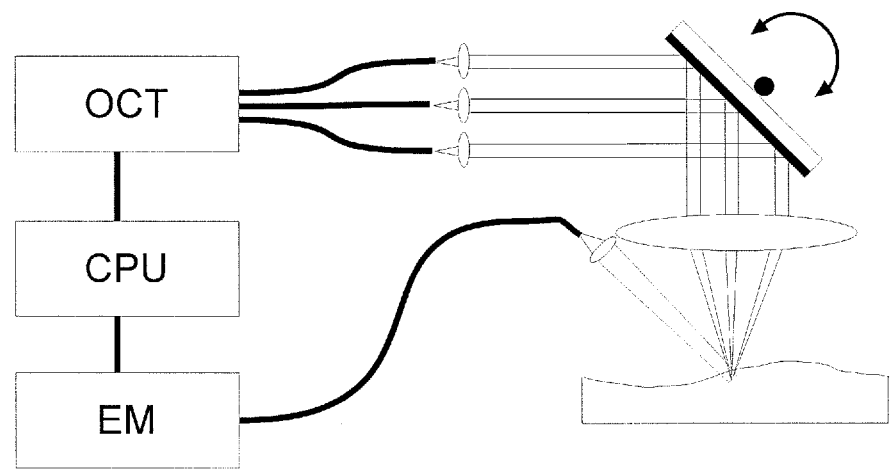
FIG. 4 shows a modified draft of the device from FIG. 3, now designed for detecting three linear independent components of the local velocity field in the heated sample.

The FD-OCT detects the spectral intensity distribution of the interference light I(k,t) (here $k=2\pi/\lambda$ is the wave number of a measurement light component, t is the time). In step b., this distribution is preferably subjected to a complex Fourier transformation according to $\int I(k,t) \exp(ikz) \, dk$, and there results the scattering strength S(z,t) as the absolute value and $\phi(z,t)$ as the phase of the Fourier coefficients. Here z refers to the local coordinate along the irradiation or backscatter direction of the measurement light. Conventionally, it is set up at right angles to the tissue surface, but this is not necessary. An inclined angle of the measurement light can also be appropriate (see for example FIG. 4 and explanations thereto).

From the so-called Doppler OCT it is known that the derivative of the phase with respect to time is a measure for the local velocity component of the scatterer in the direction of the beam, i.e. $d\phi/dt \sim v(z,t)$. In practice, instead of the differential quotient, the difference quotient $\Delta y/\Delta t$ with a $\Delta t$ that is not too small is calculated since there are numerous sources of interference during the measurement that entail a statistic phase noise. If $\Delta t$ were too small, this informationless noise would be overemphasized numerically, i.e. the signal noise ratio where unfavorable. On the other hand, $\Delta t$ may at most be only so big that the optical path length to the local scatterer at a predetermined wavelength (e.g. FD-OCT white light 820±40 nm) and a predetermined velocity does not move by more than half the wavelength (here e.g. 410 nanometers) during the interval $\Delta t$. Otherwise, the phases would change by more than $\pi$ which would not be detected during the measurement. A corresponding false estimation of the scatterer velocities would result. Thus values $t_{min}$ and $t_{max}$ exist for which $t_{min} < \Delta t < t_{max}$ must hold so that a stable measurement of the scatterer velocity can be conducted at the measurement site from the phases. Here $t_{min}$ is a function of the specific measuring device, in particular its noise behavior, while $t_{max}$ is a function of the mean measuring-light wavelength and the maximum scatterer speed to be expected. To reduce the outlay in terms of measurement (as few A scans as possible), $\Delta t$ will preferably be selected in the vicinity of $t_{max}$.

For measuring tissue velocities up to 100 µm/s for example it is sufficient to take and evaluate A scans in intervals of $\Delta t=5$ ms. $\Delta t$ should be reduced if higher velocities are to be expected.

During the FD-OCT measurement from FIG. 1, scattering strengths, phases, and tissue velocities are measured at predetermined time steps, while laser irradiation takes place at the same time. The irradiated area is marked with a wide arrow (EM). At the time when FIG. 1 was produced, a laser power of 94 mW has already been applied for approximately 500 ms. The white line labeled RPE marks the course of the RPE layer that absorbs a large part of the laser light, as is known. Two vertical white lines mark selected depth profiles 10 and 20 along which the measuring data are shown in more detail in FIG. 2. Here the depth profile 10 is at the center of the laser irradiation, however the depth profile 20 is outside the illuminated spot.

FIGS. 2a) and b) show the scattering strengths for the profiles 10 and 20. Practically no difference can be detected in these, i.e. it is difficult to discriminate between irradiated and non-irradiated tissue just on the basis of the scattering strengths.

The graphics in FIG. 2c) and d) show the instantaneous tissue velocities determined from the phases for the profiles 10 respectively 20. The laser irradiation can be determined from the markedly higher velocities (up to 40 µm/s) in profile 10. However, here too it cannot be detected in which steps which fraction of the irradiated energy depth is absorbed. The negative sign of the velocity means that the tissue moves toward the plane z=0 at the retina surface. It is thus moving closer to the radiation direction as can be expected as a result of the expansion.

The instantaneous tissue velocity—calculated by forming the difference of the phases between two subsequent A scans—is usually stochastically noisy, also contains constituents of additional oscillations, is influenced by own movements in the case of living tissue and does not allow any difference to be detected between elastic and persistent effects.

In contrast, the time integral that is described below as a displacement field D, is a hardly noisy average, the integration also acting as a low-pass filter. The displacement field D is nothing more than the actual displacement of scattering points in the tissue due to the absorption of electromagnetic radiation as a function of time and the coordinate z in the radiation direction.

In principle, $D(z,t)$ is a vector field, but only the vector component in the z direction can be measured. The time integral can be formed between any points in time. As the start of the integration, preferably a time prior or during the onset of the absorption irradiation will be selected and a time after switching off the radiation source as the integration end.

Figure 2:
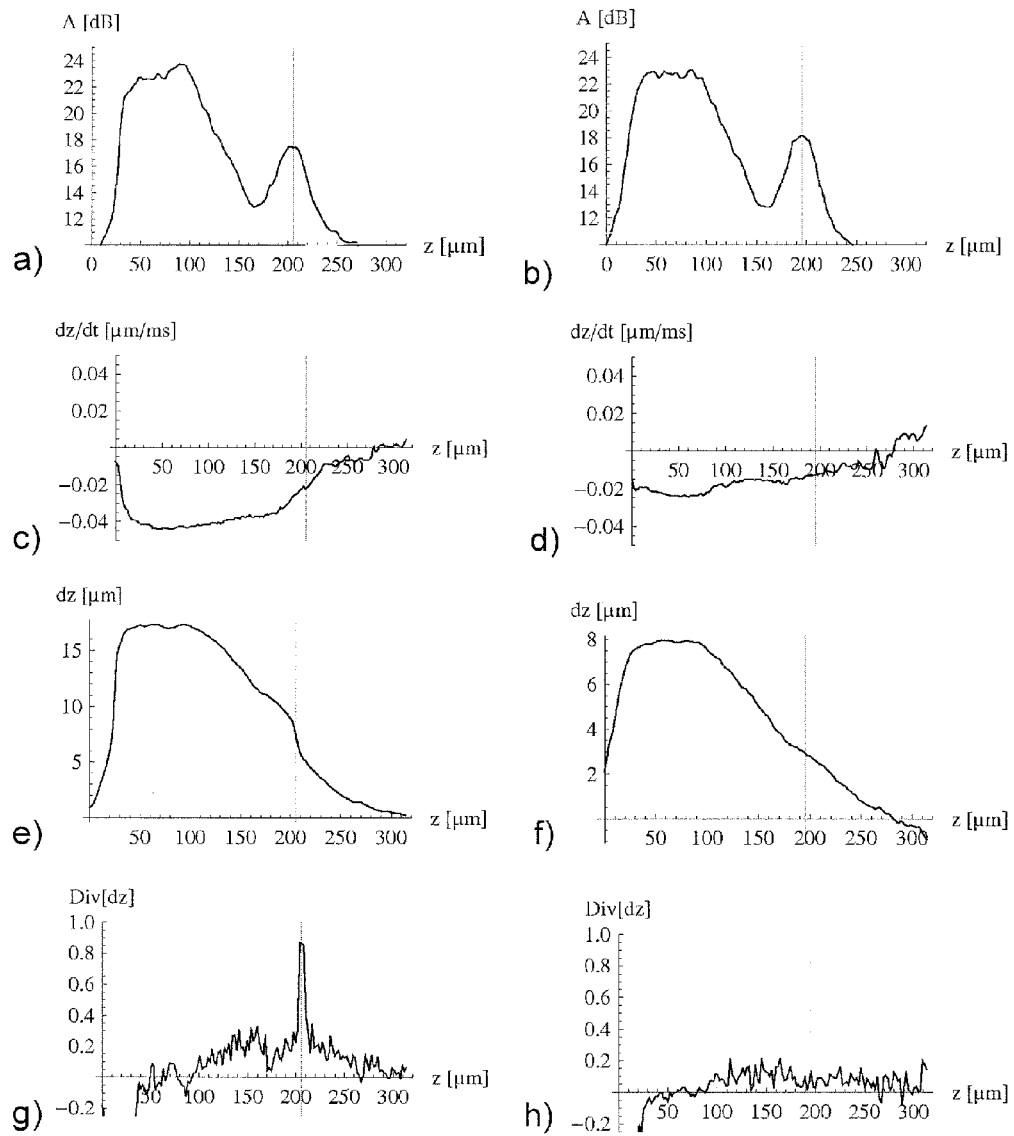
FIG. 2 shows plots of different measured and calculated quantities along the depth axis for the selected profiles from FIG. 1.

FIGS. 2e) and f) show the z components of the displacement fields in the profiles 10 respectively 20. A steep shoulder in FIG. 2e) can already be seen at a defined depth of approximately 200 µm below the retina surface. If both displacements are differentiated with respect to the depth coordinate z, the difference between irradiated and non-irradiated tissue will become particularly obvious as the graphs FIG. 2g) respectively h) show. In all graphs of FIG. 2, a vertical line shows the position of the maximum from FIG. 2g).

At each point in time t, the difference quotient $[D(z+\Delta z, t)-D(z,t)]/\Delta z$ is the change in distance of two points that originally were apart by a distance $\Delta z$. It therefore follows for infinitesimal $\Delta z$ that the derivative $dD/dz$ specifies the linear tissue expansion $\epsilon(z,t)=dD(z,t)/dz$. In the case of a purely thermoelastic expansion of the tissue (reversible expansion, no denaturing or similar), the temperature increase in the tissue can be concluded directly therefrom.

$$\epsilon(z,t)=\alpha_L(T)\,\Delta T \qquad (1)$$

Here $\alpha_L$ is the linear coefficient of thermal expansion—usually also a function of the temperature—, and $\Delta T$ the increase in temperature. For biological tissue and also for water, the coefficients of expansion are known. If only volumetric expansion coefficients $\alpha_v$ are known, you can manage using the approximation for isotropic media $\alpha_L \approx \alpha_v/3$.

To the extent that the energy deposited in the tissue by absorbing electromagnetic radiation is not sufficient to bring about the change in the tissue, the inventive device permits the spatially resolved thermoelastic tissue expansion (or contraction) to be measured directly and the depth-resolved temperature distribution along a scan line in the radiation direction also indirectly. The data thus obtained are always snapshots at the time t.

Advantageously, the measuring-light beam can be guided in a scanning manner and in a manner known per se across a tissue area. This enables a multiplicity of A scans to be carried out on a predetermined grid of the tissue surface (B scan, along the x and y coordinate axes). It is known to summarize the measuring data of all A scans and thus to obtain a three-dimensional image of the tissue.

Figure 3:
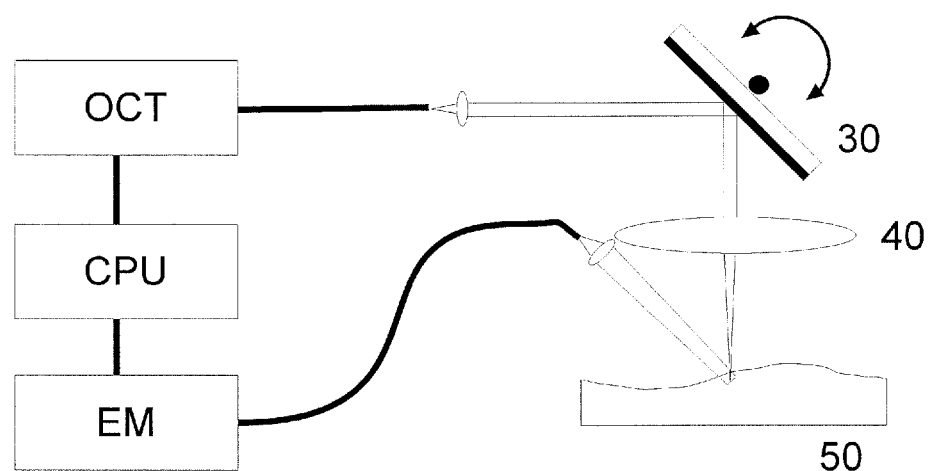
FIG. 3 shows a draft of the device comprising an FD-OCT apparatus (OCT), an electromagnetic radiation source (EM) for irradiating and locally heating a sample and a computational unit (CPU) and also a deflection device for the FD-OCT measurement light.

An exemplary embodiment for an inventive device for carrying out B scans is illustrated in FIG. 3. The polychromatic measurement light originates from a light source that is integrated into the FD-OCT apparatus (OCT). It is guided through a fiber, collimated at the exit end, and directed to a periodically swivable deflection mirror (30). This mirror guides the measurement light to an imaging optics (40) that focuses it onto the sample surface (50). During the movement of the deflection mirror (30), the focus runs across the sample (50). The FD-OCT apparatus (OCT) also comprises the means for superimposing the light back-scattered from the sample with a reference light beam and for detecting the interference light according to the prior art. The measured data of the FD-OCT apparatus (OCT) are provided for analysis and recording purposes to the computational unit (CPU) via a data line indicated in FIG. 1. The computational unit (CPU) for example compiles the measured data for a full cycle of the movement of the deflection mirror (30) as a B scan data set indexed by the measurement site of the sample and the time, and stores it on completion. It calculates the scattering strengths and phases from the FD-OCT measured data, forms the differences between the phase data of subsequent B scans (differentiating with respect to time for calculating the local velocity component), sums these phase differences cumulatively (integrating with respect to time for calculating the local displacement component $D(x,y,z,t)$) and differentiates the respectively updated time integral with respect to the depth coordinate. The spatial derivative likewise updated after completion of each B scan describes the linear expansion $\epsilon(x,y,z,t)$ of the sample (50) in the irradiation direction as a function of the measurement site on the sample surface, the depth in the sample, and the time.

FIG. 1 furthermore shows the electromagnetic radiation source (EM) whose light is guided via its own fiber and irradiated separately onto the sample. The radiation source (EM) here comprises also the control unit for controlling the irradiation parameters that, as is usual according to the prior art, is integrated structurally with the actual light source. In FIG. 1, a data link is provided between the radiation source (EM) and the computational unit (CPU). Across this data link, the computational unit (CPU) can be poll the set irradiation parameters and/or predetermine changed irradiation parameters and thus drive the radiation source (EM).

Hardly any limitations are contemplated for the radiation emitted by the radiation source (EM). It only has to be absorbed in the sample (50, here: living tissue). The entire electromagnetic spectrum below the x-rays can be envisaged here. Pulsed or cw radiation is possible, and monochromatic or polychromatic light can likewise be used. In particular even the FD-OCT measurement light radiation can itself serve to heat the tissue if a high intensity is irradiated. Normally the intensity of the FD-OCT measurement light is too low to be of any appreciable influence on the tissue.

Irradiating electromagnetic energy for the purpose of heating the tissue by absorption is usually done in a targeted manner and limited to a small area (spot). This holds in particular for laser therapy. The area that is thus of interest is usually limited to the surroundings of this spot. The inventive device therefore preferably has a scanner for deflecting the FD-OCT measurement light that exhibits a scan area with a spot as the center. This could be promoted constructively also in that the applicator for the radiation to be absorbed is rigidly connected to the scanner which is fed the measurement light via the light-conducting fibers. As an alternative, the scanner can also have a wavelength-selective design and the measurement light can be mirrored into the beam path of the therapy beam so that it deflects only the wavelength range of the measuring-light radiation while the therapeutically active radiation (e.g. microwaves) passes the scanner without being deflected.

The scanner can be an area scanner or a line scanner. Here a line scanner preferably sweeps across the center of the spot.

Mapping the tissue expansion in the z direction $\partial D(x,y,z,t)/\partial z$ onto the temperature distribution in the living tissue is possible as long as only thermoelastic movements take place. $\partial D/\partial z$ is a measured value that is sufficient to evaluate the tissue expansion as long as the micromechanic isotropy of the tissue can be assumed.

Advantageously, one does not necessarily have to rely on the isotropy assumption. Because the inventive device described so far always measures the component of the displacement field along the irradiation direction, a preferred design can be seen in the provision of plurality of simultaneous, non-parallel measuring-light beams. In particular in the case of simultaneous oblique irradiation from three linear independent directions, it is also possible to measure three linear independent components of the displacement field.

FIG. 2 shows a design of the invention where as the only difference from FIG. 1 it is provided that the FD-OCT measurement light exits the three parallel-oriented fibers in a collimated manner and hits the deflection mirror. Here the three fibers are to form the vertices of a triangle. Thus light from each fiber reaches another point of the imaging optics and is deflected toward the measuring site. In effect, the three measuring-light beams are then irradiated onto each measuring site from three linear independent directions and in the process only a single scanner is needed to collectively guide all measuring-light beams across the sample. The different irradiation directions can as an alternative also be realized by using three fibers that are oriented differently relative to the sample and are thus fixed and guide the measurement light and irradiate the sample directly (not shown). However, always to guide these beams simultaneously across the same area on the sample would be more complex. Here it is not imperative to operate three FD-OCT systems in parallel. Rather the measurement light can be guided cyclically through each of the three fibers at a fixed clock rate. For example, another fiber can be activated after each completed B scan.

The use of fibers is not necessary so that the foregoing is not to be regarded as a limitation. As is known, each fiber-guided optical setup can also be realized without fibers. Usually this is simply impractical.

The FD-OCT measurement from three linear independent spatial directions results in a few registration problems which are pointed out here. On the one hand, all measurement data are obtained in advance in an oblique coordinate system. On the other hand, individual velocity components are always obtained simultaneously along one of these coordinate axes. Due to the quantization of the scanning by the measuring-light scanner there will usually be only a few voxels of the sample volume for which two or even three components of the velocity field are measured directly. And even then the different components are moreover determined at different points in time. The numeric outlay would have to be considerable to determine the complete velocity field as a function of locus and time by three-dimensional interpolation with reasonable accuracy. To carry out the invention, luckily the task is simpler since the integration with respect to time eliminates the need for an interpolation along the time axis. In the case of the locus registration however, interpolations (of the time integrals, that is of the displacements) are expedient, and it is to be noted that it is not for all voxels of the sample that all three components of the displacement field exist at all. Outside a section volume that is penetrated by all three depth scans, corresponding measurement data are lacking. Therefore the section volume of interest should be stipulated with a sufficient size and the measurement data that are not located therein should be removed from the evaluation.

When all three components of the displacement field are measured the divergence of the displacement field $D(x,y,z,t)$ can also be calculated for non-isotropic samples. It specifies the three-dimensional tissue expansion due to the absorption of electromagnetic radiation.

$$\epsilon(x,y,z,t) = \text{div } D(x,y,z,t) = \alpha_v(T) \Delta T \quad (2)$$

In physics, the divergence of a field has the meaning of its source strength. It is invariant with respect to translations of the field. Thus own movements of the living tissue are eliminated from the measurement to the extent that they concern the tissue in question as a whole. Only expansions due for example to the blood pulse in the capillaries inside the tissue in question are still detected. However, they are characterized by a characteristic frequency (approximately 1 Hz) and can be isolated as such.

The temporal behavior of the divergence of the displacement field can likewise be interpreted physically. The following statements hold both for the three-dimensional measurement and for the one-dimensional measurement, described in the introduction, of the tissue expansion. Here it is explained how step g. of the tasks, mentioned at the start, of the computational unit is to be accomplished.

If electromagnetic radiation is applied to an absorbing volume, its temperature initially increases in a linear manner. Part of the irradiated energy is transported into the surroundings by thermal diffusion as soon as a sufficiently high temperature gradient exists that enables effective heat transport. The increase in the temperature at the absorption locus diminishes on continued radiation. Using the heat-conduction theory, the temporal course of the temperature at an unchanged absorber volume can be predicted precisely if the absorption capacity and the heat-diffusion constant are known (locally). Inversely, both values can be calculated from the temporal course of the measured temperature distribution if it is guaranteed that the tissue does not experience any irreversible changes (e.g. phase transitions, denaturing).

If the electromagnetic radiation is irradiated into the tissue with a dosage that surely is not sufficient for triggering irreversible tissue changes, then the tissue expansion $\epsilon$=div D that is to be measured with respect to time is a direct measure, if equation (2) is applied, for the depth or spatially resolved dynamic temperature increase that is achieved and using a heat-conduction model permits conclusions to be drawn as to the depth or spatially resolved absorption capacity and the heat-diffusion constant.

Using these tissue parameters, the computational unit of the inventive device can now calculate a prediction of the temperature field that would have to result if the power of the treatment radiation is increased by a predetermined increment. It then instructs the control unit of the radiation source to carry out corresponding settings to realize this increment (e.g. increase in intensity, elevating the pulse rate of a pulsed laser or the like). At the end of the following scan of the FD-OCT device, the computational unit makes an update of D, $\epsilon$=div D and of the modeled temperature field and compares the latter with the prediction.

If the differences between determined and predicted temperature distribution are within tolerable limits (due to measurement uncertainties), the next prediction is made on the basis of the instant measurement and the control device is provided with a further increment command. If however differences show up to an extent that can no longer be explained by measurement uncertainties, then it is to be assumed that additional expansions or contractions due to tissue changes have taken place in the tissue, in particular protein denaturing can be considered as a cause for this. In addition, the tissue then locally changes its optical properties, in particular scattering and absorption capacity, so that the onset of such changes leads to marked deviations from the prediction—that is only based on heat conduction in an inert medium.

That such deviations occur can give grounds to terminate the treatment radiation. Here the computational unit has available not only a physically founded termination criterion, and not only an empirical one, but over and above this also a snapshot of the tissue expansion at the time of the onset of the tissue change that is probably saved immediately. This enables a precise analysis of the tissue damage obtained, even at a later stage.

For the purpose of dosimetry check, it is advisable to set the therapeutic radiation source at the start of the irradiation to parameters that surely cannot cause any damage in the tissue. Not until sufficient data for a stable temperature modeling are available to the computational unit after a starting phase does it makes sense to increase the therapeutically active radiation dosis in steps. The increment already mentioned expressly also is to include the case of constant irradiation parameters in the next temporal step. The increment of the power of the therapeutic radiation is thus equal or greater than zero.

To realize or activate the dosimetry check as described above is optional. The inventive device can simply also be used to measure or to map the tissue parameters previously mentioned. The device is therefore a therapeutic and a diagnostic apparatus. The electromagnetic radiation source, whose radiation is absorbed in the living tissue for the purpose of local heating, is requisite in both applications for precisely controlling the energy deposition. It is an important aspect of the invention that this energy deposition takes place directly into the region monitored by the FD-OCT scan.

Finally, reference is to be suitable made to an expansion possibility of the invention. It concerns the case of the three-dimensional FD-OCT measurement, that is if all three components of the vector field D(x,y,z,t) are determined. As has already been discussed, due to the registration problems this possibility will require that B scans are performed to penetrate a predetermined section volume with depth scans. A vector-value data field across a three-dimensional volume is thus available. It enables the rotation of D to be calculated in this volume, that is the vorticity of the displacement field.

Vortices in the displacement field D correspond to local twists of the tissue if it expands under the action of the electromagnetic radiation. Such twists are always to be expected when the absorption capacity of the tissue varies strongly locally and the heating of neighboring areas takes place at different rates, the radiation performance remaining the same. In particular vortices parallel to the tissue surface have to be expected.

Determining rot D still represents a possibility in particular for short-term radiation expositions where heat diffusion does not yet play any role and div D~$\Delta$T~t is still a good approximation, to examine the spatially resolved absorption capacity of the tissue (that for example in the retina can vary laterally) if mechanical parameters like the modulus of elasticity or the shear modulus are known for example from ex vivo measurements or can be transmitted. If however the absorption capacity is assumed to be predetermined (for example from the observation, described further above, of the temporal behavior of the temperature), in vivo measurements precisely of these micromechanic parameters can be carried out where strong differences in the absorption permit this.

In summary, the present invention teaches to translate phase information of an FD-OCT system from a measurement area in a living tissue, that is being heated locally during the measurement by absorbing electromagnetic radiation, into local and instantaneous tissue velocities, to integrate these with respect to time to calculate a displacement field which itself has to be differentiated thereafter with respect to space, so that an observable—in particular the tissue expansion or the local tissue twist—is obtained. The steps that are essential for the invention can be carried out at the requisite speed only with the use of computers and thus necessarily have to be integrated into a device.

The observables are measured non-contacting in a purely optical manner. The observable is free from translations by own movements of the living sample in the measurement area. Using the means of the invention, the observable can be recorded spatially resolved and as a function of time. The observable exhibits a temporal behavior that can be interpreted physically, that permits the application of theoretical concepts and models, in particular the heat-conduction theory, so that predictions can be made under certain assumptions as to its temporal development. The onset of these predictions can be monitored and significant deviations from the predictions point to a violation of the assumptions that have been made. If this is the case, the irradiation of the tissue can be deactivated. The dosimetry check of the inventive device is thus based on monitoring the predictability of the effects caused by the therapeutic radiation.

If no dosimetry check of the radiation to be absorbed is desired or is necessary since the radiation dosage for tissue damage is selected too low anyway, then that observable is in addition suited for determining physical tissue parameters, such as absorption capacity, thermal conduction or shear modulus in vivo and in real time.

The invention claimed is:

1. A device for examining or treating living tissue by means of local heating of the tissue by absorbing electromagnetic radiation, comprising:
at least one electromagnetic radiation source adapted to emit electromagnetic radiation,
a control unit adapted to control the irradiation parameters of the radiation source, and
at least one FD-OCT apparatus with a light source adapted to deliver a measurement light to light the living tissue in the area of the absorption of the electromagnetic radiation,
a computational unit adapted to:
determine, based on the phase information of the FD-OCT interference light, the depth-resolved tissue velocity for a predetermined measuring site on the tissue and along a predetermined irradiation direction of the measurement light,
integrate the determined tissue velocity with respect to time,
differentiate the calculated time integral with respect to space, and
display the spatial derivative as a function of space and time and/or provide the spatial derivative as a function of space and time to an evaluation module and/or the control unit.

2. The device according to claim 1, wherein the computational unit is adapted to calculate a one-dimensional displacement field of the tissue as a time integral, and to calculate the linear tissue expansion as a derivative of said displacement field with respect to the coordinate of the irradiation direction of the measurement light.

3. The device according to claim 1, characterized by a controllable deflection unit for the FD-OCT measurement light, wherein the controllable deflection unit is adapted to sweep the measurement light beam across that area of the tissue that surrounds the site of maximum heating by the radiation source.

4. The device according to claim 1, further comprising optical means adapted to irradiate the tissue with the FD-OCT measurement light from at least three linear independent directions.

5. The device according to claim 4, wherein the computational unit is adapted to calculate a three-dimensional displacement field of the tissue as a time integral, and to calculate the volumetric tissue expansion as the divergence of said displacement field.

6. The device according to claim 4, wherein the computational unit is adapted to calculate a three-dimensional displacement field of the tissue as a time integral, and to calculate the local tissue twisting as the rotation of said displacement field.

7. The device according to claim 2, wherein the computational unit is adapted to store coefficients of thermal expansion of the tissue, and to determine a temperature distribution from the tissue expansion.

8. The device according to claim 7, wherein the computational unit is adapted to store absorption coefficients and thermal conductance values of the tissue, and to predict, from a temperature distribution present in a time step and given predetermined irradiation parameters, the temperature distribution to be expected in at least the next time step.

9. The device according to claim 8, wherein the computational unit is adapted to control the control unit of the radiation source and to effect a change in the irradiation parameters as a function of the deviation between measured and expected temperature distribution.

10. A method for examining or treating living tissue by means of local heating of the tissue by absorbing electromagnetic radiation, comprising:
emitting electromagnetic radiation from an electromagnetic radiation source,
controlling irradiation parameters of the radiation source, and
delivering a measurement light to the living tissue in an area of absorption of the electromagnetic radiation,
determining, based on phase information of the FD-OCT interference light, a depth-resolved tissue velocity for a predetermined measuring site on the tissue and along a predetermined irradiation direction of the measurement light,
integrating the determined tissue velocity with respect to time,
differentiating the calculated time integral with respect to space, and
displaying the spatial derivative as a function of space and time and/or providing the spatial derivative as a function of space and time to an evaluation module and/or a control unit that is controlling the irradiation parameters.

11. The method according to claim 10, further comprising:
calculating a one-dimensional displacement field of the tissue as a time integral, and
calculating linear tissue expansion as a derivative of said displacement field with respect to a coordinate of the irradiation direction of the measurement light.

12. The method according to claim 10, further comprising:
using a controllable deflection unit for the FD-OCT measurement light to sweep the measurement light beam across that area of the tissue that surrounds a site of maximum heating by the radiation source.

13. The method according to claim 10, further comprising:
irradiating the tissue with the FD-OCT measurement light from at least three linear independent directions.

14. The method according to claim 13, further comprising:
calculating a three-dimensional displacement field of the tissue as a time integral, and
calculating a volumetric tissue expansion as a divergence of said displacement field.

15. The method according to claim 13, further comprising:
calculating a three-dimensional displacement field of the tissue as a time integral, and
calculating a local tissue twisting as the rotation of said displacement field.

16. The method according to claim 10, further comprising:
storing coefficients of thermal expansion of the tissue, and
determining a temperature distribution from the tissue expansion.

17. The method according to claim 16, further comprising:
storing absorption coefficients and thermal conductance values of the tissue, and
predicting from a temperature distribution present in a time step and given predetermined irradiation parameters, a temperature distribution to be expected in at least a next time step.

18. The device according to claim 17, further comprising:
controlling the control unit of the electromagnetic radiation source to effect a change in the irradiation parameters as a function of a deviation between measured and expected temperature distribution.

* * * * *

UNITED STATES PATENT AND TRADEMARK OFFICE
CERTIFICATE OF CORRECTION

PATENT NO. : 8,774,904 B2  Page 1 of 1
APPLICATION NO. : 13/642212
DATED : July 8, 2014
INVENTOR(S) : Reginald Birngruber et al.

It is certified that error appears in the above-identified patent and that said Letters Patent is hereby corrected as shown below:

In the Specification

Column 4,
Line 51, "i.e. $d\phi/dt \sim v(z,t)$." should read --i.e. $d\varphi/dt \sim v(z, t)$.--.

Column 4,
Line 52, "quotient $\Delta y/\Delta t$" should read --quotient $\Delta\varphi/\Delta t$--.

Signed and Sealed this
Sixteenth Day of December, 2014

Michelle K. Lee
*Deputy Director of the United States Patent and Trademark Office*